United States Patent [19]
Jonkman

[11] Patent Number: 5,858,009
[45] Date of Patent: Jan. 12, 1999

[54] MULTI-LUMEN CANNULA

[75] Inventor: Kenneth R. Jonkman, Grand Rapids, Mich.

[73] Assignee: Medtronic, Inc., Minneapolis, Minn.

[21] Appl. No.: 911,334

[22] Filed: Aug. 14, 1997

[51] Int. Cl.$^6$ .................................................... A61M 5/00
[52] U.S. Cl. ........................... 604/264; 604/282; 604/49
[58] Field of Search ................................ 604/49, 52, 53, 604/43, 44, 264, 280–282

[56] References Cited

U.S. PATENT DOCUMENTS

| | | |
|---|---|---|
| 3,734,083 | 5/1973 | Kolin . |
| 4,451,252 | 5/1984 | Martin . |
| 4,543,087 | 9/1985 | Sommercorn et al. . |
| 4,675,004 | 6/1987 | Hadford et al. . |
| 5,160,325 | 11/1992 | Nichols et al. . |
| 5,348,536 | 9/1994 | Young et al. . |
| 5,374,245 | 12/1994 | Mahurkar . |
| 5,451,206 | 9/1995 | Young . |
| 5,554,136 | 9/1996 | Luther . |
| 5,569,182 | 10/1996 | Twardowski et al. . |

*Primary Examiner*—John D. Yasko
*Attorney, Agent, or Firm*—Foley & Lardner

[57] ABSTRACT

The multi-lumen cannula according to the invention is preferably formed from two separate sub-cannulas, a portion of which are adhered to one another. Preferably, the adhered portions of the sub-cannulas are deformed such that the assembled multi-lumen cannula is substantially circular in cross section throughout the adhered portions of the sub-cannulas. In addition, the septum separating the multiple lumens of the cannula is preferably reinforced so that the multi-lumen cannula can accommodate dramatically different fluid pressure within the cannula without deformation of the septum. This cannula is ideally suited for use in a variety of left-heart and right-heart assist cardiac surgical procedures, especially minimally invasive procedures.

82 Claims, 8 Drawing Sheets

MULTI-LUMEN CANNULA

BACKGROUND OF THE INVENTION

1. Field of the Invention

This invention relates to multi-lumen cannulas and, more particularly, to a reinforced multi-lumen cannula having staggered lumen fluid outlets spaced along the length of the cannula making a cannula ideally suited for use in a variety of cardiac surgical procedures.

2. Description of the Related Art

Cannulas have long been used in a variety of applications to inject or withdraw fluid from the body. It is known to create a single lumen cannula having wire reinforcement integrated in the body of the cannula to provide enhanced rigidity and avoid kinking of the cannula. It is also known to create a cannula having multiple lumens provided therein for delivering a variety of fluids and medications into and out of the body. However, one significant problem which exists in the art is the creation of a single cannula having multiple lumens formed therein wherein each lumen is independently reinforced so that the cannula can accommodate dramatically different fluid pressures in the adjacent cannulas without risk of collapsing the septum separating the different lumens.

Cannulas are often used in cardiac surgical procedures to conduct fluid to and from the various chambers of the heart and vessels conducting fluid to and from the heart. One desirable goal of a cardiac surgical procedure is to minimize the number of incisions which are formed in the heart and the vessels leading to and from the heart. It is especially important to minimize the number of incisions in the aorta in view of the significant fluid pressures which are experienced by this vessel during normal beating of the heart.

SUMMARY OF THE INVENTION

The cannula according to the invention overcomes the problems of the prior art by providing a multi-lumen cannula with independently reinforced lumens so that dramatically different fluid pressures can be accommodated in the same multi-lumen cannula. In addition, the cannula according to the invention achieves some of the desirable goals of cardiac surgery by minimizing the number of incisions which must be created in the heart and the vessels leading to and from the heart.

In a first aspect, the multi-lumen cannula according to the invention comprises at least two lumens formed in the cannula. The lumens have proximal and distal ends and fluid inlet and outlet apertures. A septum is provided which separates the first and second lumens from one another. The septum is reinforced to resist deflection of the septum in response to fluid pressure differentials in the adjacent lumen. With this structure, dramatically different fluid pressures can be accommodated in the two adjacent lumens without deflection of the septum into the lower pressure lumen.

In the preferred embodiment, the lumens are wire reinforced. In another aspect of the invention, the multi-lumen cannula is an assembly of a first sub-cannula and a second sub-cannula. Each of the sub-cannulas has a proximal end, a distal end, and a lumen extending between the ends. Once again, apertures are formed in the lumens to accommodate the flow of fluid therethrough. A portion of the first sub-cannula is adhered to a portion of the second sub-cannula to create a septum separating the lumens of the two sub-cannulas. Once again, the preferred embodiment of the septum includes wire reinforcement to resist deflection of the septum and thereby accommodate varying fluid pressure levels inside the lumens.

In still another aspect of the invention, the multi-lumen cannula comprises an assembly of two sub-cannulas substantially similar to those described above. However, in this embodiment, the adhered portion of the first and second sub-cannulas are non-circular in cross section wherein the non-adhered portions of the sub-cannulas are substantially circular in cross section. Preferably, the cross-section of the adhered portion of the multi-lumen cannula is substantially circular. With this structure, the cannula can be easily inserted through an incision while minimizing trauma to the tissue which the cannula encounters. This structure is ideally suited for insertion into the body through access ports used during a minimally invasive surgical procedure.

In the preferred embodiment, the non-circular portions of the sub-cannulas are D-shaped in cross section and, when assembled to one another, result in a substantially circular cross section. Another aspect of the invention is directed to a method of assisting fluid flow in the cardiovascular system. This method comprises the steps of providing a multi-lumen cannula similar to one of the embodiments described above. The cannula is inserted into the vascular system of a patient so that the distal fluid aperture of the first sub-cannula is received in a first heart chamber or vessel, and the distal fluid aperture of the second sub-cannula is received in a second heart chamber or vessel fluidly communicating with the heart. Once the cannula has been so positioned, the proximal fluid apertures of the first and second sub-cannulas are connected to a pump or other means for conducting fluid through the two sub-cannulas. Utilizing this method, the multi-lumen cannula according to the invention can be used in a left-heart assist operation, a right-heart assist operation or two multi-lumen cannulas can be used for both left- and right-heart assist operations.

Still another aspect of the invention is directed to the method of forming the multi-lumen cannula substantially as described above. This method comprises the steps of providing two sub-cannulas, both of which are substantially circular in cross section. Next, at least a portion of each of the sub-cannulas is deformed to create a non-circular portion. Finally, the non-circular portion of the first cannula is adhered to the non-circular portion of the second sub-cannula. In the preferred embodiment, a portion of the subcannulas are formed in the D-shaped configuration which, when assembled, results in a substantially circular cross section for the adhered portion of the multi-lumen cannula.

BRIEF DESCRIPTION OF THE DRAWINGS

The invention will now be described with reference to the drawings in which.

DETAILED DESCRIPTION OF THE PREFERRED EMBODIMENTS

Figure 1:
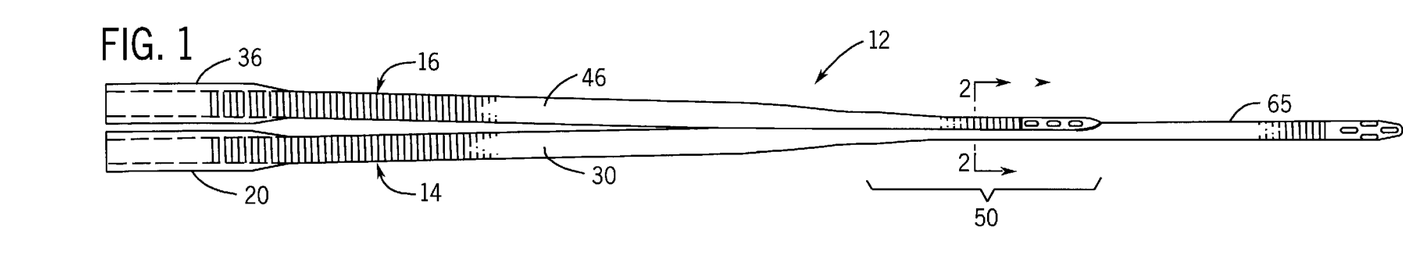
FIG. 1 is a top, plan view of a multi-lumen cannula according to the invention.
Figure 2:
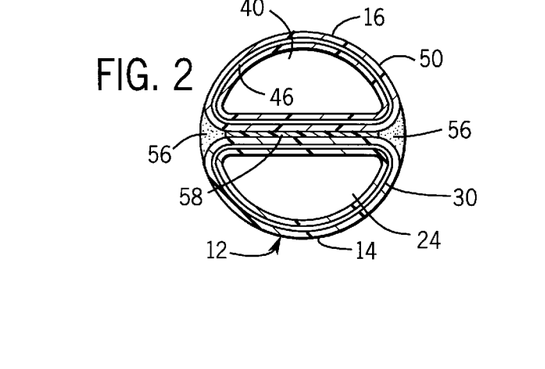
FIG. 2 is a cross-sectional view of the multi-lumen cannula taken along lines 2—2 of FIG. 1.
Figure 3:
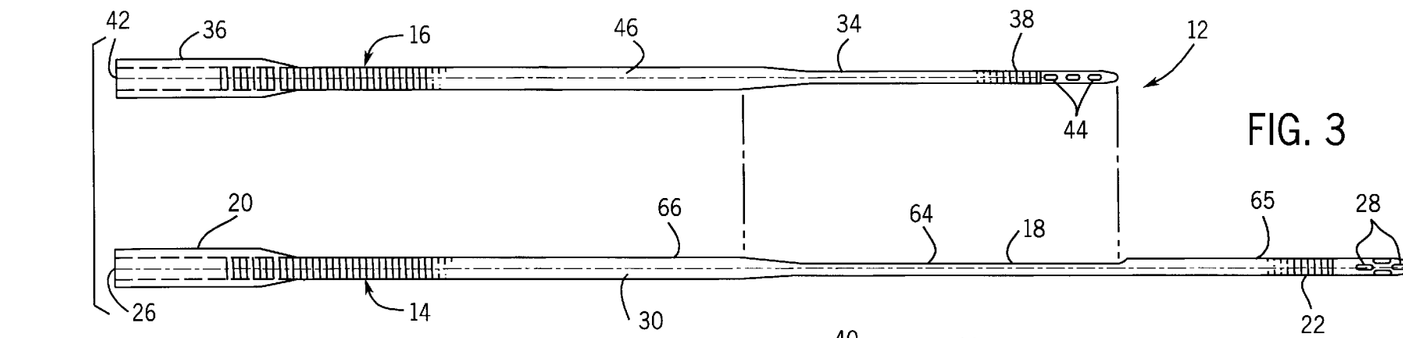
FIG. 3 is an exploded, top, plan view of the multi-lumen cannula of FIG. 1.

Referring now to drawings and to FIGS. 1–3 in particular, a multi-lumen cannula 12 according to the invention is shown. The multi-lumen cannula 12 comprises a first sub-cannula 14 and a second sub-cannula 16 which are mounted to one another to create the multi-lumen cannula 12. The first sub-cannula 14 comprises a wire reinforced body portion 18 having a proximal end 20 and a distal end 22. A lumen 24 extends from a proximal lumen aperture 26 provided on the proximal end 20 to at least one distal lumen aperture 28 provided at the distal end 22. The body portion 18 is formed of a flexible material acceptable for use inside the human body, preferably polyvinyl chloride. Preferably, the body portion 18 includes some form of reinforcing to provide radial rigidity to the cannula and to prevent kinking of the cannula during deformation. The preferred means of reinforcement comprises a conventional helical wire 30 imbedded in the body portion 18.

The structural elements of the second sub-cannula 16 are substantially identical to those of the first sub-cannula and include a body portion 34, a proximal end 36, a distal end 38, a lumen 40, a proximal lumen aperture 42, at least one distal lumen aperture 44, and a reinforcing wire 46.

In the preferred embodiment, the first sub-cannula 14 is longer than the second sub-cannula 16, and the second sub-cannula 16 is secured to the first sub-cannula 14 such that the proximal ends 20, 36 are immediately adjacent one another and the distal ends 22, 38 are spaced from one another. Further, the distal end 22 of the second sub-cannula 16 and a portion of the body immediately adjacent the distal end 22 is securely adhered to the body 18 of the first sub-cannula 14. The adhered portion 50 of the two sub-cannulas is dimensioned and designed to avoid any sharp corners or contours and provide a smooth transition along the exterior surface, without adversely affecting the flow rate through the lumens of the two sub-cannulas. These features are achieved by deforming portions of the sub-cannulas utilizing a die similar to that seen in FIGS. 4 and 5.

Figure 4:
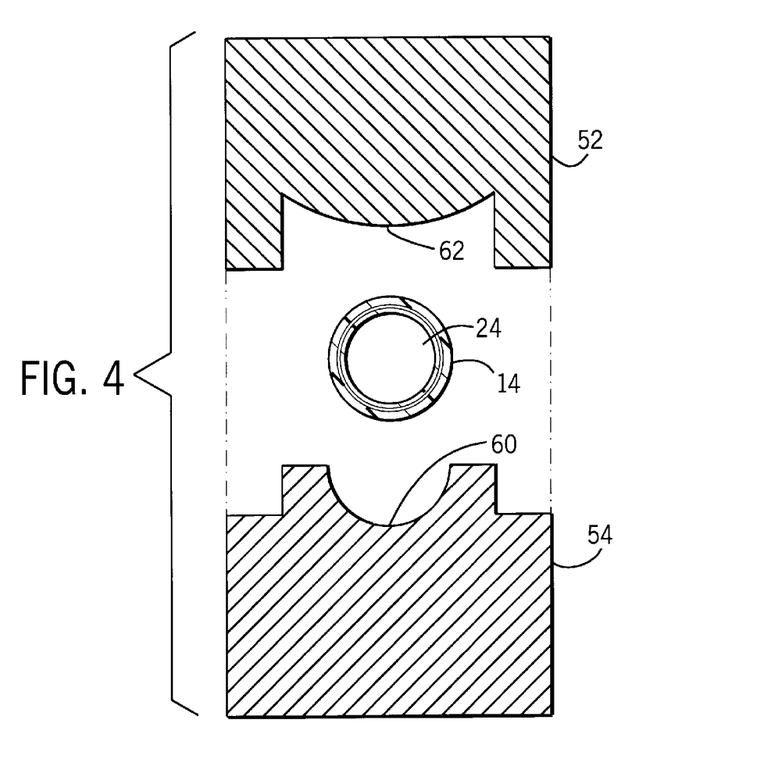
FIG. 4 is a sectional view of a die assembly used in the manufacture of the multi-lumen cannula, the die assembly being adapted to deform a sub-cannula.
Figure 5:
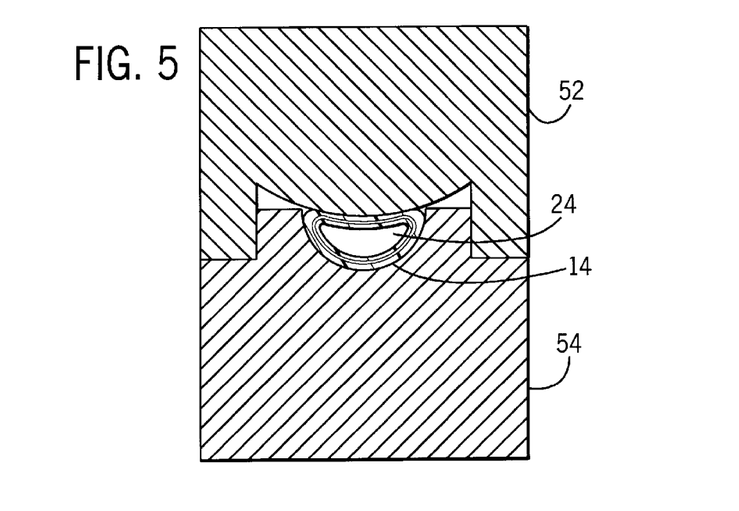
FIG. 5 is a sectional view of the die assembly of FIG. 4 showing the die assembly in the closed position.

The portions of the first and second sub-cannulas 14, 16 which comprise the adhered portion 50 are preferably D-shaped in cross section and secured to one another so that the flat portions of the D-shape are adjacent one another, thereby creating a substantially circular, assembled cross section as seen in FIG. 2. The D-shaped contour is formed by inserting a portion of the sub-cannulas between a pair of opposed dies and then closing the dies to deform the sub-cannulas and create the desired shape. The preferred embodiment of the dies are seen in FIGS. 4 and 5 and comprise an upper, convex die 52 and a lower, concave die 54. As seen in FIG. 4, a portion of the sub-cannula 14 is positioned between the opposed dies 52, 54. Next, the dies 52, 54 are closed, as seen in FIG. 5. The molding surface 60 of the concave lower die 54 is substantially complimentary to the contour of the undeformed sub-cannula 14. Therefore, the portion of the sub-cannula received in this portion of die retains substantially the same contour as prior to deformation. The molding surface 62 of the upper die 52 is preferably convex and deforms a portion of the reinforced sub-cannula 14 to deflect inwardly into the lumen 24 of the sub-cannula. The memory of the wire 30 utilized in the sub-cannula 14 is such that the convex portion 52 of the deformed sub-cannula will spring back to a substantially planar condition as seen in FIG. 2. In other words, in order to achieve the D-shaped contour of the sub-cannula 14 as seen in FIG. 2, it is preferred to use a convex die 52 to overcome the memory of the materials forming the reinforced sub-cannula. While experimentation has shown that it is preferred to use the combination of a convex and concave die, it may be possible to utilize a concave die and a substantially planar die, depending upon the selection of materials and the response of the materials to the deforming operation.

During conventional manufacturing operations, substantially the entire length of the first and second sub-cannulas are circular in cross section prior to deformation in the dies 52, 54. As seen in FIG. 1, it is preferred that only an intermediate portion 64 of the first sub-cannula 14 is deformed into the D-shaped configuration, a body portion 65 distally from the D-shaped portion 64 remains circular in cross section as does the body portion 66 proximately from the D-shaped portion 64. It is preferred that only a portion of the body adjacent the distal portion of the second sub-cannula 18 be deformed into the D-shaped configuration. The two deformed D-shaped portions are secured to one another by a conventional adhesive 56 to create the adhered portion 50 of the multi-lumen cannula 12. It is preferred that an adhesive be used which will fill any gaps in the adhered portion 50 to create a substantially smooth, exterior surface for the adhered portion 50.

The preferred embodiment of the adhesive used is known as Dymax 191 M adhesive which is manufactured by Dymax Corporation located in Torrington, Conn. This is a light curing adhesive which fills the gaps to create a smooth contour on the exterior surface of the multi-lumen cannula. Any adhesive which is essentially non-shrinking and preferably uses little or no evaporating solvents can be used.

The preferred embodiment of the multi-lumen cannula spaces the distal lumen apertures of the first and second sub-cannulas from one another. With this configuration, the multi-lumen cannula is ideally suited for use in a variety of cardiac surgical procedures which will be described in greater detail below. However, it is to be understood that the multi-lumen cannula 12 according to the invention can be adapted for a wide variety of applications and uses such that the proximal lumen apertures of the two sub-cannulas can be positioned immediately adjacent one another or spaced a variety of distances from one another. In addition, the multi-lumen cannula 12 according to the invention utilizes a pair of sub-cannulas which are D-shaped in cross section. It is understood by persons skilled in the art that the multi-lumen cannula according to the invention can incorporate more than two sub-cannulas merely by changing the contour of the die and the adhered portion. For example, three or more wedge- or pie-shaped sub-cannulas can be mounted to one another according to the invention.

One key aspect of the preferred embodiment of the multi-lumen cannula according to the invention is the fact that reinforcement is provided in the septum 58 which separates the lumens of the two sub-cannulas. This reinforced septum provides significant advantages over previous multi-lumen cannulas because the cannula 12 can now accommodate dramatically different fluid pressure levels inside the immediately adjacent lumens. For example, significant positive fluid pressure can be created in one of the lumens while a significant negative fluid pressure is created in the adjacent lumen. Prior multi-lumen cannulas could not accommodate such varying pressure levels in adjacent lumens because the septum would deflect and quickly pinch closed the lower pressure lumen. The reinforced septum of the multi-lumen cannula according to the invention is a significant improvement in the art. In the preferred embodiment, each of the flat portions of the sub-cannulas are independently reinforced, resulting in a septum 58 which can resist deflection despite dramatically different fluid pressure levels in the adjacent lumens. However, it is understood that a multi-lumen cannula according to the invention could be constructed wherein only one of the several sub-cannulas is reinforced.

Figure 6:
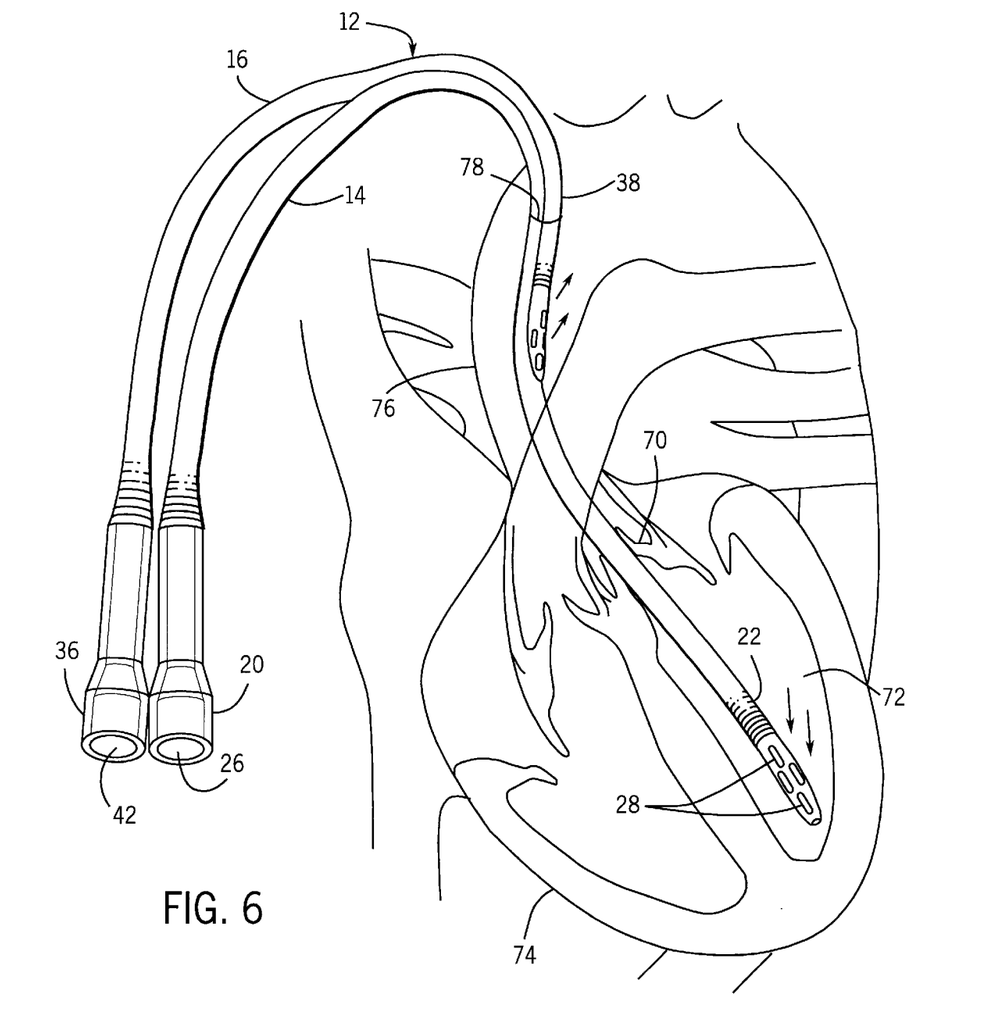
FIG. 6 is a schematic view of the multi-lumen cannula in a first operative position positioned in the human heart passing through the arctic valve.

The multi-lumen cannula 12 according to the invention, as seen in FIG. 1, can be used in a variety of applications to conduct fluid into and out of the human body. However, the lumen 12 is ideally suited for use in cardiac surgical procedures. As seen in FIG. 6, the cannula 12 can be used to conduct blood in a human vascular system across the aortic valve 70. In this first operative position, the distal lumen apertures 28 of the first sub-cannula 14 are positioned in the left ventricle 72 of the heart 74, and the distal lumen apertures 44 of the second sub-cannula 16 are positioned in the aorta 76 downstream from the aortic valve 70. With this structure and position, a single incision 78 is formed in the aorta to accommodate the fluid flow paths for withdrawing blood from the left ventricle and simultaneously supplying blood to the aorta 76. Previously, two incisions were required to accomplish both of these functions. The fluid withdrawn from the left ventricle through the first sub-cannula 14 will likely be at a lower fluid pressure than the blood supplied to the aorta 76 through the second sub-cannula 16. The reinforced septum 58 can accommodate these differing fluid pressures without deforming and altering the cross-sectional area of the lumens 24, 40.

In the first operative position as seen in FIG. 6, the proximal end 20 of the first sub-cannula 14 is fluidly connected to a pump or some other mechanism for withdrawing blood from the left ventricle 72, and the proximal end 36 of the second sub-cannula 16 is fluidly connected to the outlet of this pump.

Figure 7:
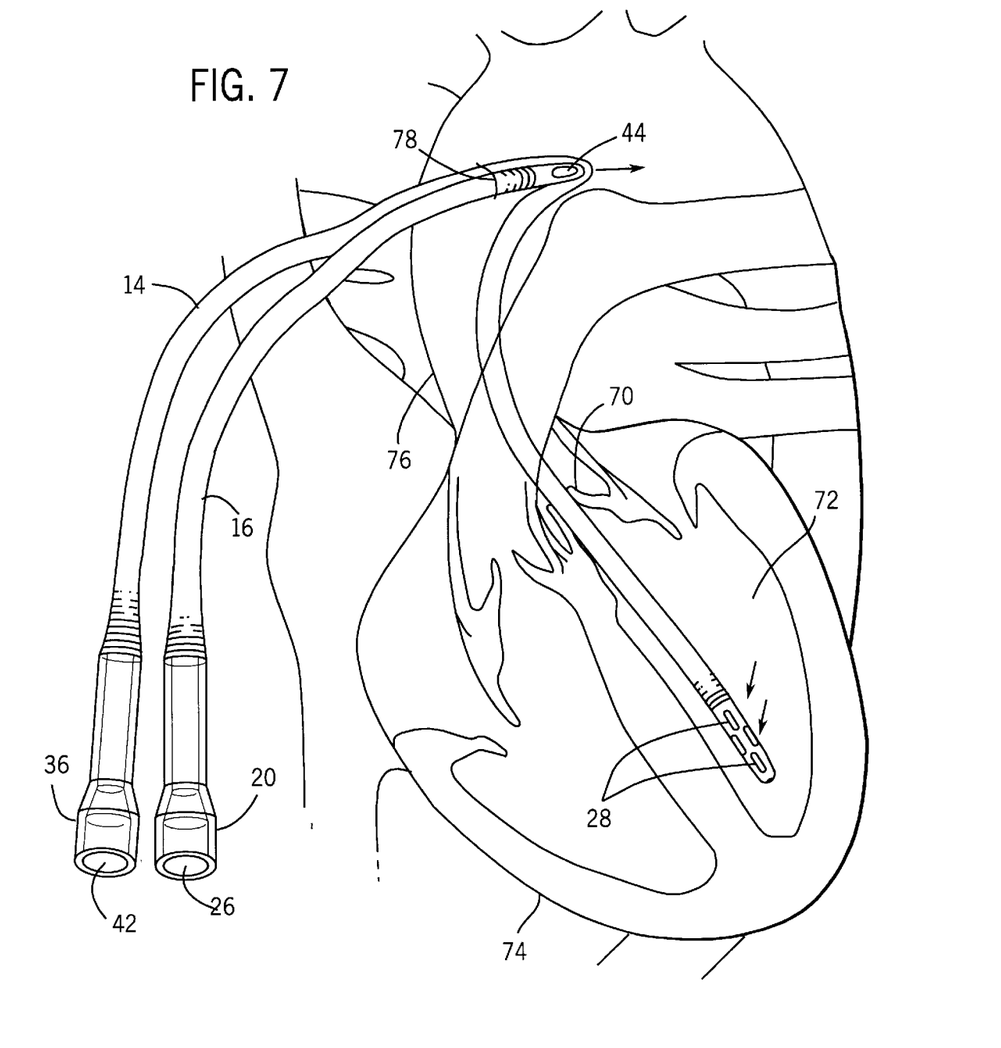
FIG. 7 is a schematic view of the multi-lumen cannula in a second operative position positioned in the human heart passing through the aortic valve.

FIG. 7 shows the multi-lumen cannula 12 according to the invention in a second operative position. Similar to the positioning shown in FIG. 6, the distal lumen apertures 28, 42 of the sub-cannulas 14, 16 are positioned on opposite sides of the arctic valve 70. However, the incision 78 has been repositioned on the aorta 76 closer to the valve 70.

Figure 8:
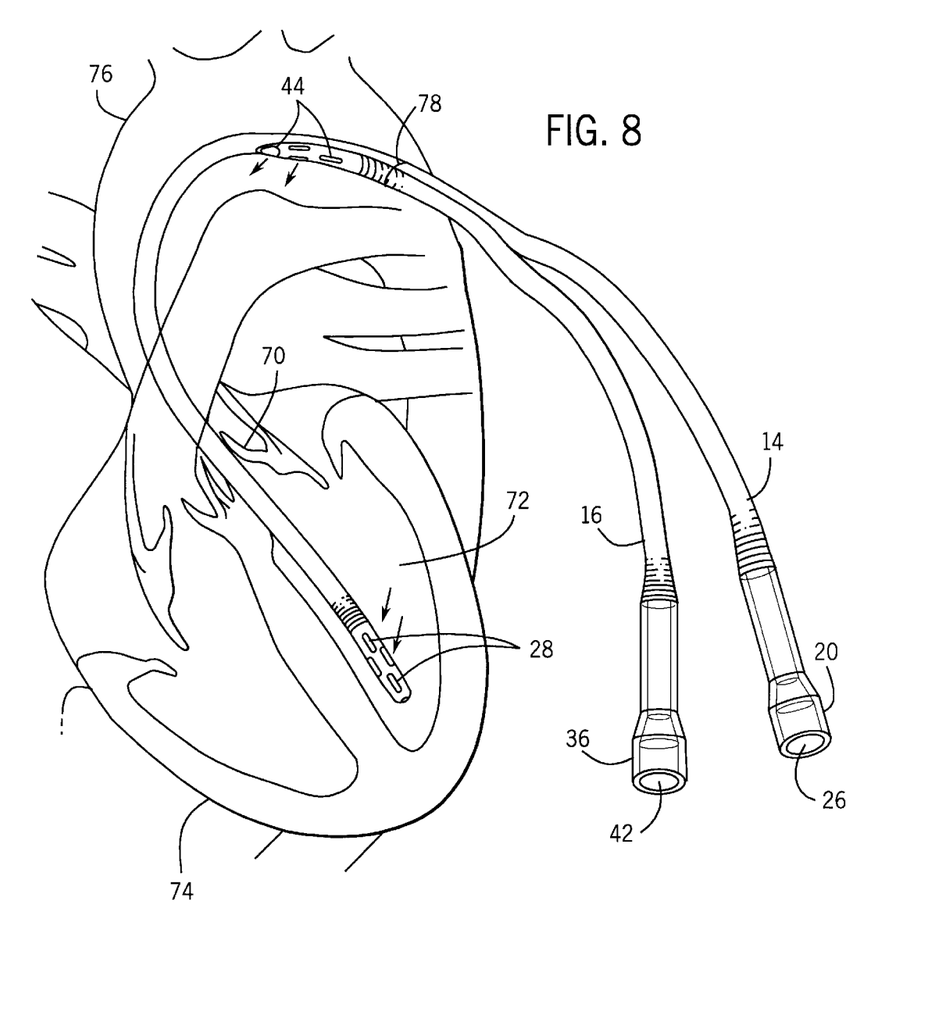
FIG. 8 is a schematic view of the multi-lumen cannula in a third operative position positioned in the human heart passing through the aortic valve.

FIG. 8 is a schematic drawing of a third operative position for the multi-lumen cannula 12 according to the invention. Similar to the positions seen in FIGS. 6 and 7, the distal lumen apertures 28, 42 are positioned on opposite sides of the arctic valve and the incision 78 has been positioned further downstream from the earlier applications.

Figure 9:
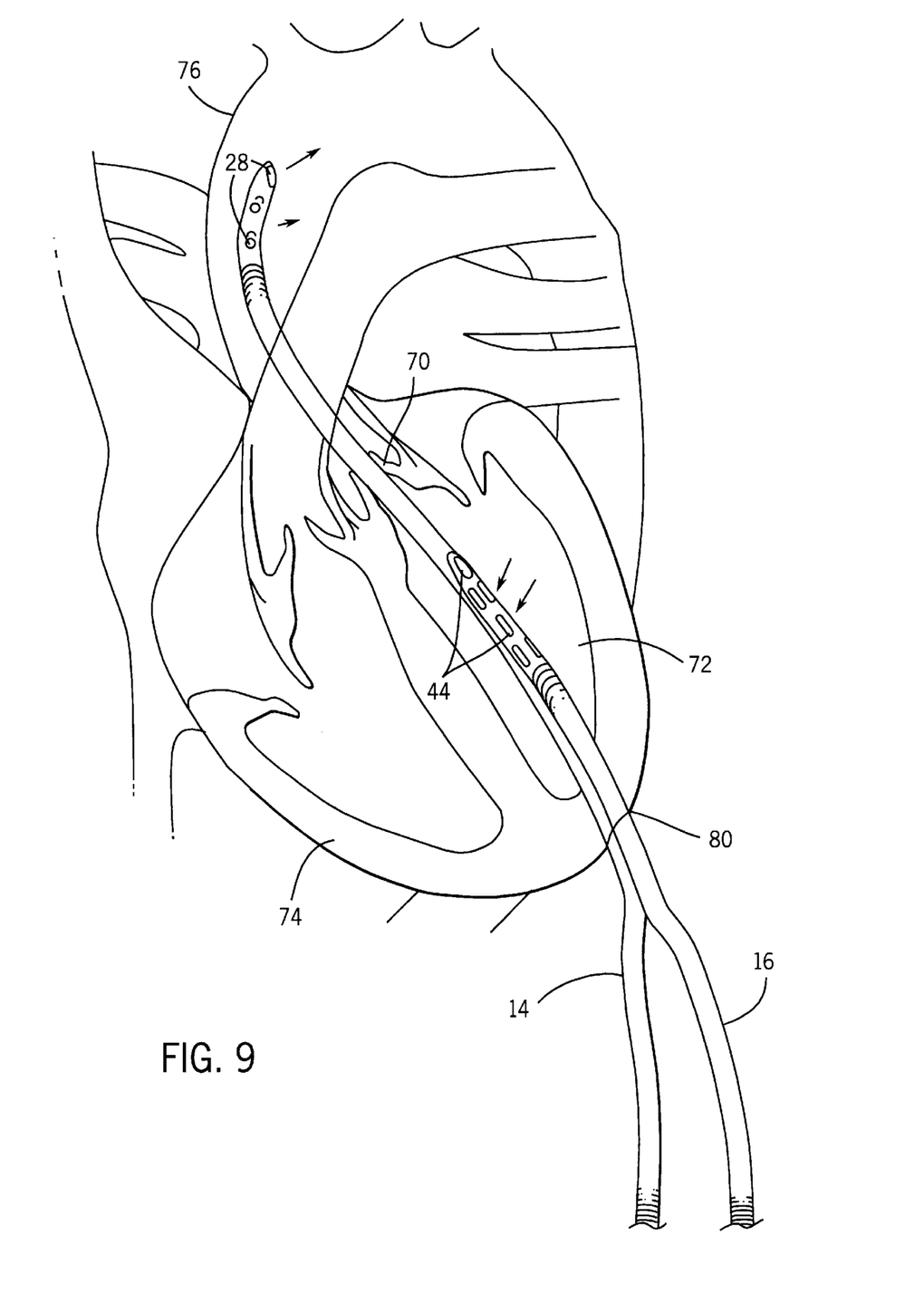
FIG. 9 is a schematic view of the multi-lumen cannula in a fourth operative position positioned in the human heart passing through the aortic valve.

FIG. 9 shows the multi-lumen cannula 12 in a fourth operative position which, similar to the earlier operative positions, shows the distal lumen apertures 28, 42 on opposite sides of the arctic valve 70. However, in this position, the cannula 12 is inserted through an incision 80 formed directly in the wall of the left ventricle 72. In this position, blood is withdrawn from the left ventricle 72 through the distal lumen aperture 44 of the second sub-cannula 16, and the blood is discharged into the aorta 76 through the distal lumen aperture 28 of the first sub-cannula 14. As is evident from the various applications seen in FIGS. 6–9, the preferred embodiment of the multi-lumen cannula according to the invention is ideally suited to provide left-heart assist.

Figure 10:
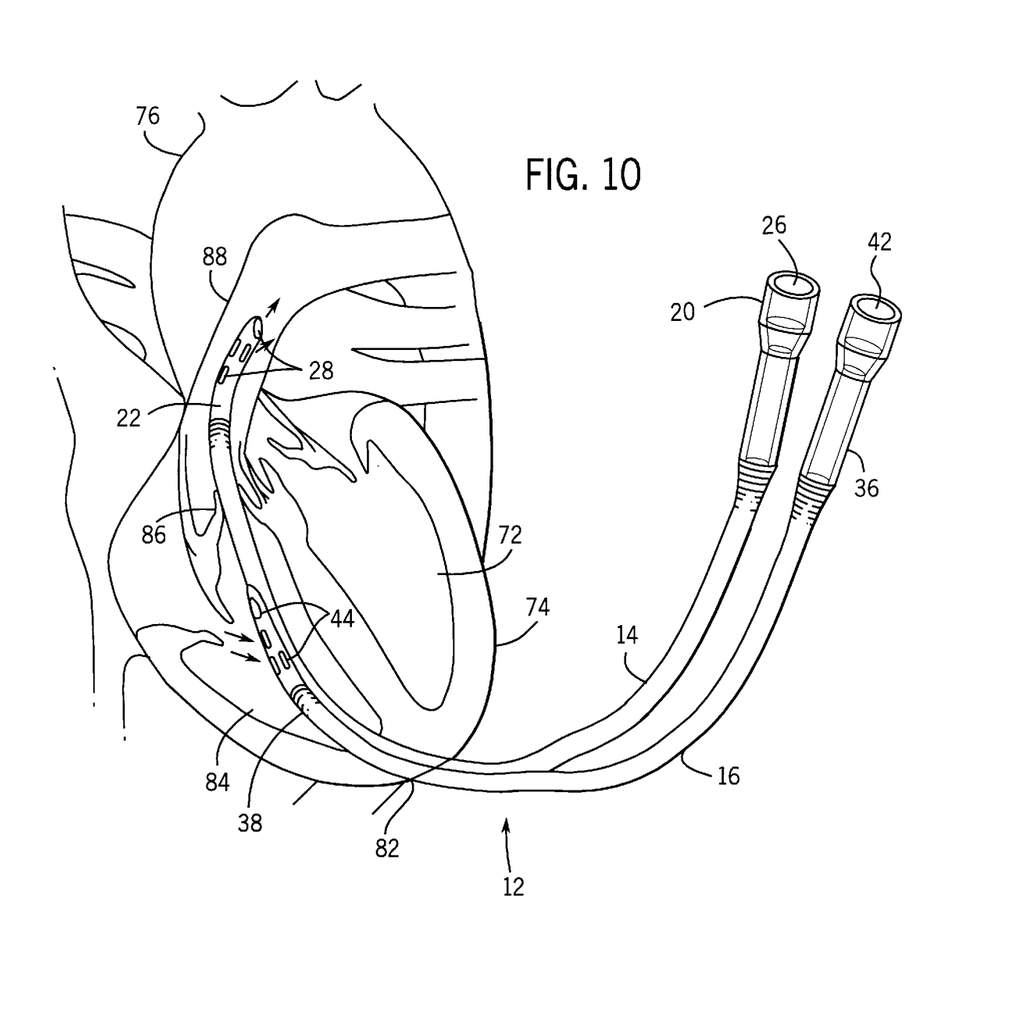
FIG. 10 is a schematic view of the multi-lumen cannula in a fifth operative position positioned in the human heart passing through the pulmonary valve.
Figure 11:
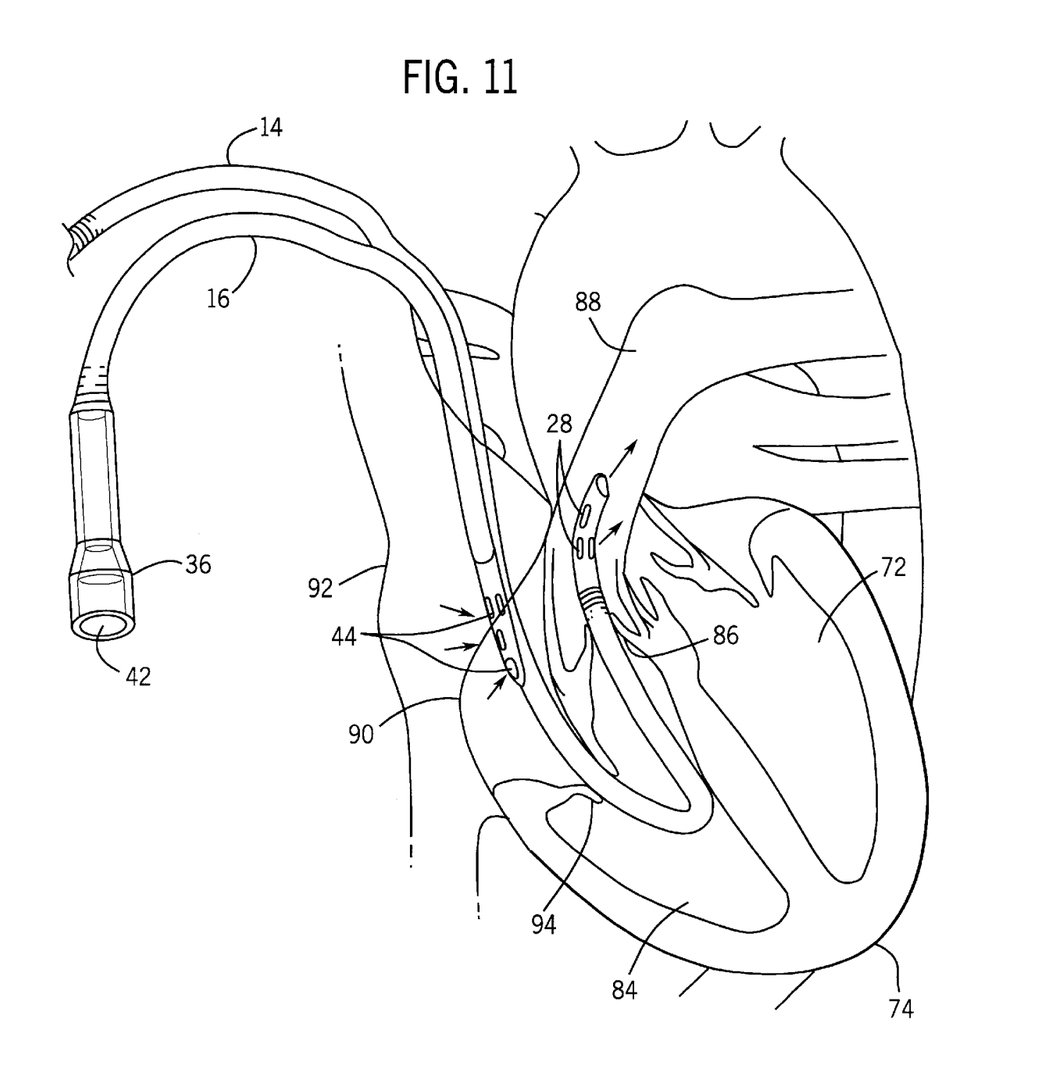
FIG. 11 is a schematic view of the multi-lumen cannula in a sixth operative position positioned in the human heart passing through both the tricuspid valve and pulmonary valve.

FIGS. 10 and 11 show use of the multi-lumen cannula 12 according to the invention for right-heart assist procedures. As seen in FIG. 10, the multi-lumen cannula 12 has been inserted into the heart 74 through an incision 82 formed in the wall of the right ventricle 84. The distal lumen apertures 44 of the second sub-cannula 16 are positioned in the right ventricle 84 while the distal lumen apertures 28 of the first sub-cannula 14 are positioned on the other side of the pulmonary valve 86 in the pulmonary artery 88. In this operative position, the distal end 38 of the second sub-cannula 16 is fluidly connected to the inlet of a pump, and the distal end 22 of the first sub-cannula 14 is fluidly connected to the outlet of the pump (not shown).

FIG. 11 shows use of the multi-lumen cannula 12 according to the invention in a sixth operative position. In this position, the cannula is inserted through an incision (not shown) formed in one of the right atrium 90 or the vena cava 92. The cannula is inserted past the tricuspid valve 94, through the right ventricle 84, past the pulmonary valve 86, and into the pulmonary artery 88. In this position, the blood is withdrawn from the right atrium 90 and vena cava 92 through the distal lumen apertures 44 of the second sub-cannula 16 and the blood is discharged into the pulmonary artery 88 through the distal lumen apertures 28 of the first sub-cannula 14. The distal ends of the first and second sub-cannulas 14, 16 are preferably connected to a fluid pump (not shown) to accommodate this movement of the blood in the vascular system.

FIGS. 10 and 11 show two alternative positions of the multi-lumen cannula 12 according to the invention to provide right-heart assist. It is to be understood that two different multi-lumen cannulas 12 according to the invention can be used simultaneously to provide both right and left-heart assist functions. For example, a first multi-lumen cannula can be positioned in one of the positions seen in FIGS. 6–9 to provide left-heart assist while a second multi-lumen cannula according to the invention can be positioned as seen in one of FIGS. 10 and 11 to provide right-heart assist. Each use of the multi-lumen cannula 12 according to the invention as described above provides an advantage over the prior art by eliminating an incision in the vasculature system which, in view of the significant fluid pressures inside the system, can be a dramatic improvement over the past procedures. In addition, a single, multi-lumen cannula can be used to accommodate dramatically different fluid pressures within each of the lumens without undesirable deforming or altering the cross-sectional area of the lumens.

Reasonable variation and modification are possible within the spirit of the foregoing specification and drawings without departing from the scope of the invention.

The embodiments for which an exclusive property or privilege is claimed are defined as follows:

1. An improved multi-lumen cannula for conducting fluid to and from a body comprising a first lumen having a proximal end, a distal end, and a first and second fluid apertures spaced from one another, and a second lumen having a proximal end, a distal end and first and second fluid apertures spaced from one another, the improvement comprising:

septum separating the first and second lumens wherein the septum is wire reinforced to resist deflection of the septum.

2. An improved multi-lumen cannula according to claim 1 wherein both the first and second lumens are reinforced so that the septum separating the two lumens has greater reinforcement and resistance to deflection as compared to either of the lumens.

3. An improved multi-lumen cannula according to claim 2 wherein the lumens are wire reinforced.

4. An improved multi-lumen cannula according to claim 1 wherein one of said two fluid apertures for each of the first and second lumens are positioned adjacent one another along the axial length of the multi-lumen cannula.

5. An improved multi-lumen cannula according to claim 4 wherein the other of said two fluid apertures for each of the first and second lumens are spaced from one another along the axial length of the multi-lumen cannula.

6. An improved multi-lumen cannula according to claim 1 wherein one of said two fluid apertures for each of the first and second lumens are spaced from one another along the axial length of the multi-lumen cannula.

7. An improved multi-lumen cannula according to claim 1 wherein only a portion of the first and second lumens are adhered to one another and the remainder of the first and second lumens are free relative to one another.

8. An improved multi-lumen cannula according to claim 7 and further comprising a gap filling adhesive used to bind the two adhered portions of the lumens to one another.

9. An improved multi-lumen cannula according to claim 7 wherein the adhered portions of each of the two lumens are substantially D-shaped in cross section.

10. An improved multi-lumen cannula according to claim 9 wherein the free portions of the two lumens are substantially circular in cross section.

11. A multi-lumen cannula assembly comprising:
a first sub-cannula comprising a proximal end, a distal end, a lumen extending between the proximal and distal ends, proximal and distal fluid apertures formed in the lumen, and reinforcement to resist radial deflection of the lumen;
a second sub-cannula comprising a proximal end, a distal end, a lumen extending between the proximal and distal ends, and proximal and distal fluid apertures formed in the lumen, a portion of the first sub-cannula being adhered to a portion of the second sub-cannula to create a septum separating the lumens of the first and second sub-cannulas, wherein the reinforcement of the lumen of the first sub-cannula resists deflection of the septum as a result of differing fluid pressure levels inside the lumens.

12. A multi-lumen cannula according to claim 11 wherein the adhered portion of the first sub-cannula is non-circular in cross section and the non-adhered portion of the first sub-cannula is substantially circular in cross section.

13. A multi-lumen cannula according to claim 12 wherein the adhered portion of the first sub-cannula is D-shaped in cross section.

14. A multi-lumen cannula according to claim 12 wherein the adhered portion of the second sub-cannula is non-circular in cross section and the non-adhered portion of the second sub-cannula is substantially circular in cross section.

15. A multi-lumen cannula according to claim 14 wherein the adhered portion of the second sub-cannula is D-shaped in cross section.

16. A multi-lumen cannula according to claim 15 wherein the adhered portion of the first sub-cannula is D-shaped in cross section.

17. A multi-lumen cannula according to claim 11 wherein the first sub-cannula is wire reinforced.

18. A multi-lumen cannula according to claim 17 wherein the second sub-cannula is wire reinforced.

19. A multi-lumen cannula according to claim 11 wherein distal fluid apertures of the lumens of the first and second sub-cannulas are spaced from one another along the axial length of the multi-lumen cannula.

20. A multi-lumen cannula according to claim 19 wherein proximal fluid apertures of the lumens of the first and second sub-cannulas are adjacent one another along the axial length of the multi-lumen cannula.

21. A multi-lumen cannula assembly comprising:
a first sub-cannula comprising a proximal end, a distal end, a lumen extending between the proximal and distal ends, proximal and distal fluid apertures formed in the lumen, a portion of the first sub-cannula being circular in cross section and another portion being non-circular;
a second sub-cannula comprising a proximal end, a distal end, a lumen extending between the proximal and distal ends, and proximal and distal fluid apertures formed in the lumen, a portion of the second sub-cannula being circular in cross section and another portion being non-circular, the non-circular portion of the first sub-cannula being adhered to the non-circular portion of the second sub-cannula wherein the cross section of the adhered portions of the first and second sub-cannulas is substantially circular.

22. A multi-lumen cannula according to claim 21 and further comprising a septum separating the lumens of the adhered portions of the first and second sub-cannulas wherein the septum is reinforced to resist deflection of the septum with respect to the two lumens.

23. A multi-lumen cannula according to claim 22 wherein the septum is reinforced by wire.

24. A multi-lumen cannula according to claim 22 wherein the first sub-cannula is reinforced to prevent radial deflection of the lumen of the sub-cannula.

25. A multi-lumen cannula according to claim 24 wherein the second sub-cannula is reinforced to prevent radial deflection of the lumen of the sub-cannula.

26. A multi-lumen cannula according to claim 21 wherein the non-circular portion of the second sub-cannula is D-shaped in cross section.

27. A multi-lumen cannula according to claim 26 wherein the non-circular portion of the first sub-cannula is D-shaped in cross section.

28. A multi-lumen cannula according to claim 21 wherein distal fluid apertures of the lumens of the first and second sub-cannulas are spaced from one another along the axial length of the multi-lumen cannula.

29. A multi-lumen cannula according to claim 28 wherein proximal fluid apertures of the lumens of the first and second sub-cannulas are adjacent one another along the axial length of the multi-lumen cannula.

30. A method of assisting fluid flow in the cardiovascular system comprising the steps of:
providing a multi-lumen cannula comprising:
a first sub-cannula comprising a proximal end, a distal end, a lumen extending between the proximal and distal ends, and proximal and distal fluid apertures formed in the lumen, a portion of the first sub-cannula being circular in cross section and another portion being non-circular; and
a second sub-cannula comprising a proximal end, a distal end, a lumen extending between the proximal and distal ends, and proximal and distal fluid apertures formed in the lumen, a portion of the second sub-cannula being circular in cross section and another portion being non-circular, wherein the distal fluid apertures of the two lumens are spaced from one another along the axial length of the multi-lumen cannula and the non-circular portion of the first sub-cannula is adhered to the non-circular portion of the second sub-cannula so that the cross section of the adhered portions of the first and second sub-cannulas is substantially circular;

inserting the cannula into the vasculature system of a patient so that the distal fluid aperture of the lumen of the first sub-cannula is received in one of a first chamber of the heart or vessel fluidly communicating with the heart and the distal fluid aperture of the lumen of the second sub-cannula is received in one of a second chamber of the heart or vessel fluidly communicating with the heart; and fluidly connecting the proximal fluid apertures of the first and second sub-cannulas to a fluid conducting pump for moving fluid through the two sub-cannulas.

31. A method of assisting fluid flow in the cardiovascular system according to claim 30 wherein the cannula is inserted into the vasculature system through an incision formed in the aorta.

32. A method of assisting fluid flow in the cardiovascular system according to claim 31 wherein the distal fluid aperture of the first sub-cannula is received in the left ventricle.

33. A method of assisting fluid flow in the cardiovascular system according to claim 32 wherein the distal fluid aperture of the second sub-cannula is received in the aorta.

34. A method of assisting fluid flow in the cardiovascular system according to claim 30 and further comprising a septum separating the lumens of the adhered portions of the first and second sub-cannulas and further comprising reinforcement in the septum to resist radial deflection of the septum with respect to the first and second sub-cannulas.

35. A method of assisting fluid flow in the cardiovascular system according to claim 30 wherein the cannula is inserted into the vasculature system through an incision formed in the heart wall.

36. A method of assisting fluid flow in the cardiovascular system according to claim 35 wherein the distal fluid aperture of the second sub-cannula is received in the left ventricle.

37. A method of assisting fluid low in the cardiovascular system according to claim 36 wherein the distal fluid aperture of the first sub-canula is received in the aorta.

38. A method of assisting fluid flow in the cardiovascular system according to claim 35 wherein the distal fluid aperture of the first sub-cannula is received in the pulmonary artery.

39. A method of assisting fluid flow in the cardiovascular system according to claim 38 wherein the distal fluid aperture of the second sub-cannula is received in the right ventricle.

40. A method of assisting fluid flow in the cardiovascular system according to claim 38 wherein the distal fluid aperture of the second sub-cannula is received in the right atrium.

41. A method of assisting fluid flow in the cardiovascular system according to claim 30 wherein the cannula is inserted in to the vasculature system through an incision formed in the vena cava, the distal fluid aperture of the second sub-cannula is received in the right atrium and the distal fluid aperture of the first sub-cannula is received in the pulmonary artery.

42. A method of forming a multi-lumen cannula comprising the steps of:

providing a first sub-cannula having a proximal end, a distal end, a lumen extending between the proximal and distal ends, and proximal and distal fluid apertures formed in the lumen, the first sub-cannula being substantially circular in cross section;

providing a second sub-cannula having a proximal end, a distal end, a lumen extending between the proximal and distal ends, and proximal and distal fluid apertures formed in the lumen, the second sub-cannula being substantially circular in cross section deforming a portion of the first sub-cannula to create a non-circular portion;

deforming a portion of the second sub-cannula to create a non-circular portion;

adhering the non-circular portions of the first and second sub-cannulas to one another.

43. An improved multi-lumen cannula for conducting fluid to and from a body comprising a first lumen having a proximal end, a distal end, and a first and second fluid apertures spaced from one another, and a second lumen having a proximal end, a distal end and first and second fluid apertures spaced from one another, the improvement comprising:

a septum separating the first and second lumens wherein the septum is reinforced to resist deflection of the septum, wherein both the first and second lumens are reinforced so that the septum separating the two lumens has greater reinforcement and resistance to deflection as compared to either of the lumens.

44. An improved multi-lumen cannula according to claim 43 wherein the septum is wire reinforced.

45. An improved multi-lumen cannula according to claim 43 wherein the lumens are wire reinforced.

46. An improved multi-lumen cannula according to claim 43 wherein one of said two fluid apertures for each of the first and second lumens are positioned adjacent one another along the axial length of the multi-lumen cannula.

47. An improved multi-lumen cannula according to claim 46 wherein the other of said two fluid apertures for each of the first and second lumens are spaced from one another along the axial length of the multi-lumen cannula.

48. An improved multi-lumen cannula according to clam 43 wherein one of said two fluid apertures for each of the first and second lumens are spaced from one another along the axial length of the multi-lumen cannula.

49. An improved multi-lumen cannula according to claim 43 wherein only a portion of the first and second lumens are adhered to one another and the remainder of the first and second lumens are free relative to one another.

50. An improved multi-lumen cannula according to claim 49 and further comprising a gap filling adhesive used to bind the two adhered portions of the lumens to one another.

51. An improved multi-lumen cannula according to claim 49 wherein the adhered portions of each of the two lumens are substantially D-shaped in cross section.

52. An improved multi-lumen cannula according to claim 51 wherein the free portions of the two lumens are substantially circular in cross section.

53. An improved multi-lumen cannula for conducting fluid to and from a body comprising a first lumen having a proximal end, a distal end, and a first and second fluid apertures spaced from one another, and a second lumen having a proximal end, a distal end and first and second fluid apertures spaced from one another, the improvement comprising:

a septum separating the first and second lumens wherein the septum is reinforced to resist deflection of the septum, wherein one of said two fluid apertures for each of the first and second lumens are positioned adjacent one another along the axial length of the multi-lumen cannula.

54. An improved multi-lumen cannula according to claim 53 wherein the septum is wire reinforced.

55. An improved multi-lumen cannula according to claim 53 wherein both the first and second lumens are reinforced so that the septum separating the two lumens has greater reinforcement and resistance to deflection as compared to either of the lumens.

56. An improved multi-lumen cannula according to claim 55 wherein the lumens are wire reinforced.

57. An improved multi-lumen cannula according to claim 53 wherein the other of said two fluid apertures for each of the first and second lumens are spaced from one another along the axial length of the multi-lumen cannula.

58. An improved multi-lumen cannula according to clam 53 wherein one of said two fluid apertures for each of the first and second lumens are spaced from one another along the axial length of the multi-lumen cannula.

59. An improved multi-lumen cannula according to claim 53 wherein only a portion of the first and second lumens are adhered to one another and the remainder of the first and second lumens are free relative to one another.

60. An improved multi-lumen cannula according to claim 59 and further comprising a gap filling adhesive used to bind the two adhered portions of the lumens to one another.

61. An improved multi-lumen cannula according to claim 59 wherein the adhered portions of each of the two lumens are substantially D-shaped in cross section.

62. An improved multi-lumen cannula according to claim 61 wherein the free portions of the two lumens are substantially circular in cross section.

63. An improved multi-lumen cannula for conducting fluid to and from a body comprising a first lumen having a proximal end, a distal end, and a first and second fluid apertures spaced from one another, and a second lumen having a proximal end, a distal end and first and second fluid apertures spaced from one another, the improvement comprising:

a septum separating the first and second lumens wherein the septum is reinforced to resist deflection of the septum, wherein one of said two fluid apertures for each of the first and second lumens are spaced from one another along the axial length of the multi-lumen cannula.

64. An improved multi-lumen cannula according to claim 63 wherein the septum is wire reinforced.

65. An improved multi-lumen cannula according to claim 63 wherein both the first and second lumens are reinforced so that the septum separating the two lumens has greater reinforcement and resistance to deflection as compared to either of the lumens.

66. An improved multi-lumen cannula according to claim 65 wherein the lumens are wire reinforced.

67. An improved multi-lumen cannula according to claim 63 wherein one of said two fluid apertures for each of the first and second lumens are positioned adjacent one another along the axial length of the multi-lumen cannula.

68. An improved multi-lumen cannula according to claim 67 wherein the other of said two fluid apertures for each of the first and second lumens are spaced from one another along the axial length of the multi-lumen cannula.

69. An improved multi-lumen cannula according to claim 63 wherein only a portion of the first and second lumens are adhered to one another and the remainder of the first and second lumens are free relative to one another.

70. An improved multi-lumen cannula according to claim 69 and further comprising a gap filling adhesive used to bind the two adhered portions of the lumens to one another.

71. An improved multi-lumen cannula according to claim 70 wherein the adhered portions of each of the two lumens are substantially D-shaped in cross section.

72. An improved multi-lumen cannula according to claim 71 wherein the free portions of the two lumens are substantially circular in cross section.

73. An improved multi-lumen cannula for conducting fluid to and from a body comprising a first lumen having a proximal end, a distal end, and a first and second fluid apertures spaced from one another, and a second lumen having a proximal end, a distal end and first and second fluid apertures spaced from one another, the improvement comprising:

a septum separating the first and second lumens wherein the septum is reinforced to resist deflection of the septum, wherein only a portion of the first and second lumens are adhered to one another and the remainder of the first and second lumens are free relative to one another.

74. An improved multi-lumen cannula according to claim 73 wherein the septum is wire reinforced.

75. An improved multi-lumen cannula according to claim 73 wherein both the first and second lumens are reinforced so that the septum separating the two lumens has greater reinforcement and resistance to deflection as compared to either of the lumens.

76. An improved multi-lumen cannula according to claim 75 wherein the lumens are wire reinforced.

77. An improved multi-lumen cannula according to claim 73 wherein one of said two fluid apertures for each of the first and second lumens are positioned adjacent one another along the axial length of the multi-lumen cannula.

78. An improved multi-lumen cannula according to claim 77 wherein the other of said two fluid apertures for each of the first and second lumens are spaced from one another along the axial length of the multi-lumen cannula.

79. An improved multi-lumen cannula according to clam 73 wherein one of said two fluid apertures for each of the first and second lumens are spaced from one another along the axial length of the multi-lumen cannula.

80. An improved multi-lumen cannula according to claim 73 and further comprising a gap filling adhesive used to bind the two adhered portions of the lumens to one another.

81. An improved multi-lumen cannula according to claim 73 wherein the adhered portions of each of the two lumens are substantially D-shaped in cross section.

82. An improved multi-lumen cannula according to claim 81 wherein the free portions of the two lumens are substantially circular in cross section.

* * * * *

UNITED STATES PATENT AND TRADEMARK OFFICE
CERTIFICATE OF CORRECTION

PATENT NO. : 5,858,009  
APPLICATION NO. : 08/911334  
DATED : January 12, 1999  
INVENTOR(S) : Kenneth R. Jonkman Page 1 of 1

It is certified that error appears in the above-identified patent and that said Letters Patent is hereby corrected as shown below:

Column 7, line 1, that portion of the claim reading "septum" should read --a septum--.

Column 8, line 36, that portion of the claim reading "to claim 22" should read --to claim 21--.

Column 9, line 46, that portion of the claim reading "fluid low in" should read --fluid flow in--.

Column 9, line 48, that portion of the claim reading "sub-canula" should read --sub-cannula--.

Column 9, line 63, that portion of the claim reading "in to the" should read --into the--.

Column 10, line 12, that portion of the claim reading "section" should read --section;--.

Column 10, line 44, that portion of the claim reading "to clam" should read --to claim--.

Column 11, line 20, that portion of the claim reading "to clam" should read --to claim--.

Column 12, line 48, that portion of the claim reading "to clam" should read --to claim--.

Signed and Sealed this

Tenth Day of July, 2007

JON W. DUDAS  
*Director of the United States Patent and Trademark Office*